(12) United States Patent
Domankevitz

(10) Patent No.: US 10,492,862 B2
(45) Date of Patent: Dec. 3, 2019

(54) ULTRASOUND TECHNOLOGY FOR HAIR REMOVAL

(71) Applicant: LUMENIS LTD., Yokneam Ilit (IL)

(72) Inventor: Yacov Domankevitz, Zichron Yaacov (IL)

(73) Assignee: Lumenis Ltd., Yokneam (IL)

( * ) Notice: Subject to any disclaimer, the term of this patent is extended or adjusted under 35 U.S.C. 154(b) by 455 days.

(21) Appl. No.: 15/138,389

(22) Filed: Apr. 26, 2016

(65) Prior Publication Data

US 2016/0310212 A1 Oct. 27, 2016

Related U.S. Application Data

(60) Provisional application No. 62/152,987, filed on Apr. 27, 2015.

(51) Int. Cl.
*A61B 18/18* (2006.01)
*A61B 18/20* (2006.01)
(Continued)

(52) U.S. Cl.
CPC .............. *A61B 18/203* (2013.01); *A61N 7/02* (2013.01); *A61B 2018/00005* (2013.01); *A61B 2018/00476* (2013.01); *A61B 2018/00958* (2013.01); *A61B 2018/00994* (2013.01); *A61B 2018/20361* (2017.05); *A61N 2007/0034* (2013.01); *A61N 2007/0078* (2013.01)

(58) Field of Classification Search
CPC . A61B 18/18; A61B 18/20; A61B 2018/2015; A61B 2018/203; A61B 2018/00005; A61B 2018/00041; A61B 2018/00053; A61B 2018/273; A61B 2018/00291; A61B 2018/00315; A61B 2018/00452; A61B 2018/0047; A61B 2018/00476; A61B 2018/00994; A61N 5/06; A61N 5/0613; A61N 5/0616; A61N 5/0617; A61N 2005/0626; A61N 2005/0627; A61N 2005/0632; A61N 2005/0643; A61N 7/00; A61N 2007/0004; A61N 2007/0034; A61N 2007/0078
USPC ................ 606/9, 11, 27, 28; 607/88–91, 96, 607/100–102; 128/898
See application file for complete search history.

(56) References Cited

U.S. PATENT DOCUMENTS 5,968,034 A 10/1999 Fullmer
6,050,990 A * 4/2000 Tankovich ........... A61B 18/203
606/16

(Continued)

*Primary Examiner* — Ahmed M Farah
(74) *Attorney, Agent, or Firm* — ISUS Intellectual Property PLL

(57) ABSTRACT

A cosmetic method for the removal of hair from the skin tissue of a human body includes providing a device that includes a source of ultrasound energy and a source of light-based energy; activating the source of ultrasound energy and providing the ultrasound energy to the skin tissue to heat an area of skin tissue containing hair follicles from about 43 degrees C. to about 55 degrees C. for a first predetermined period of time; activating the source of light-based energy after the expiration of the first predetermined period of time to heat hair follicles in the area of skin tissue containing hair follicles to one of: above 55 degrees C., 60 degrees C., 65 degrees C. or 70 degrees C. for a second predetermined period of time.

16 Claims, 3 Drawing Sheets

(51) Int. Cl.
*A61N 7/02* (2006.01)
*A61B 18/00* (2006.01)
*A61N 7/00* (2006.01)

(56) References Cited

U.S. PATENT DOCUMENTS

| | | | |
|---|---|---|---|
| 6,200,326 B1* | 3/2001 | Narayanan | A61B 17/320068 606/133 |
| 6,595,934 B1* | 7/2003 | Hissong | A61N 7/02 601/3 |
| 7,815,633 B2* | 10/2010 | Zanelli | A61N 7/02 606/27 |
| 8,950,406 B2 | 2/2015 | Karni | |
| 9,149,331 B2* | 10/2015 | Deem | A61B 18/02 |
| 2005/0154332 A1* | 7/2005 | Zanelli | A61N 7/02 601/2 |
| 2007/0239144 A1* | 10/2007 | Korenberg | A61B 18/203 606/9 |
| 2010/0010480 A1* | 1/2010 | Mehta | A61B 18/14 606/9 |
| 2012/0029394 A1* | 2/2012 | Babaev | A61B 18/203 601/2 |
| 2012/0191085 A1* | 7/2012 | Eckhouse | A45D 26/0028 606/33 |
| 2013/0184693 A1* | 7/2013 | Neev | A61B 18/18 606/9 |
| 2014/0025050 A1* | 1/2014 | Anderson | A61N 5/0616 606/9 |
| 2015/0032128 A1* | 1/2015 | Tavlin | B26B 21/48 606/131 |
| 2017/0252105 A1* | 9/2017 | Deem | A61B 18/02 |

* cited by examiner

ULTRASOUND TECHNOLOGY FOR HAIR REMOVAL

RELATED APPLICATIONS

This application is related to and claims priority to U.S. provisional application Ser. No. 62/152,987, filed Apr. 27, 2015, the entire contents of which are herein incorporated by reference.

BACKGROUND AND RELATED ART

Hair removal devices rely on the photothermolysis principle to destroy hair follicles. This hair removal procedure often requires raising the temperature of the treated area until reaching the desired damage effect. These procedures could often prove to be painful.

Therefore, there is a great need to develop a device for hair removal that heats the hair follicle to a degree sufficient to cause damage while keeping the level of pain minimized.

Low-fluence light pulses from a coherent light source such as a laser or an incoherent light source such as from a flash lamp have been used for hair removal treatment, as described in U.S. Pat. No. 8,950,406. That patent describes delivering a series or plurality of these pulses rapidly to the treated area. The hair follicle is damaged while minimally raising the thermal energy of the epidermis. The skin temperature found to damage the hair follicle is about 45° C. while keeping the temperature of the epidermis in a range from about 42-50° C. However, this light-based technology is melanin-based, and thus only dark colored hair follicles absorb the energy of the light source.

SUMMARY OF THE INVENTION

The present invention includes an apparatus that uses ultrasound energy to damage hair follicles while providing minimal thermal energy to the treated area. Unlike light-based technology of the type described above for hair removal, ultrasound is not melanin-based and can provide the same energy to either a dark or light hair follicle. Moreover, even melanin-based hair removal methodology is inefficient for pigmented hair when it comes to fine hair like, for example, facial hair. Prior uses of ultrasound energy to either remove hair or to reduce wrinkles appear to operate in the range of 50-60 degrees C. to as much as 65 degrees C. See, for example, U.S. Pat. Nos. 6,113,559 and 7,815,633 and US Publication No. 2008/10183110. These levels are levels similar to those used in connection with light-based hair removal devices.

In an aspect, a cosmetic method for the removal of hair from the skin tissue of a human body includes providing a device that includes a source of ultrasound energy and a source of light-based energy; activating the source of ultrasound energy and providing the ultrasound energy to the skin tissue to heat an area of skin tissue containing hair follicles from about 43 degrees C. to about 55 degrees C.; continuing the providing of ultrasound energy for a first predetermined period of time; and activating the source of light-based energy after the expiration of the first predetermined period of time to heat hair follicles in the area of skin tissue containing hair follicles to one of: above 55 degrees C., 60 degrees C., 65 degrees C. or 70 degrees C. for a second predetermined period of time, wherein the second predetermined period of time is less than the first predetermined period of time.

In another aspect, the first predetermined period of time is in the range of about 1 second to about 15 minutes and the second predetermined period of time is less than about 1 second. A programmable or programmed controller is provided to control the activation of the source of ultrasonic energy and the source of light-based energy and the first and second predetermined periods of time.

In another aspect, the source of ultrasonic energy and the source of light-based energy are contained within a unitary housing, the unitary housing having a surface placed in contact with the skin tissue at least during activation of the source of ultrasonic energy and the source of light-based energy. The method may also include cooling the skin tissue with a cooling device in the unitary housing during one or more of activations of the ultrasonic energy source and the light-based energy source.

In another aspect, the surface in contact with the skin tissue is shaped to form a cavity, and a source of negative pressure draws the skin tissue into the cavity to draw the tissue closer to one or more of the source of ultrasonic energy or the source of light-based energy. An imaging device may provide images of hair follicles to be targeted by one or more of ultrasonic energy or light-based energy.

In yet another aspect, the ultrasonic source of energy may provide the energy at 200 KHz to 5 MH; the light-based source of energy is a laser energy source. The method may include measuring the temperature of the skin tissue, using one or more suitable sensors, one or more of: before, during or after the providing of one or more of ultrasonic energy or light-based energy to the skin tissue.

In a further aspect, a cosmetic method for the removal of hair from the skin tissue of a human body includes providing a device that includes no light-based source and only a source of ultrasound energy; activating the source of ultrasound energy and providing the ultrasound energy to the skin tissue to heat an area of skin tissue containing hair follicles from about 43 degrees C. to about 55 degrees C.; and, continuing the providing of ultrasound energy for a first predetermined period of time.

In yet a further aspect, an apparatus for the removal of hair from the skin tissue of a human body includes a source of ultrasound energy and a source of light-based energy; a controller programmed to activate one or more of the sources of ultrasound energy and light-based energy for first and second predetermined periods of time; the controller causes activation of the source of ultrasound energy and causing the source of ultrasound energy to be provided to the skin tissue to heat an area of skin tissue containing hair follicles from about 43 degrees C. to about 55 degrees for the first predetermined period of time; the controller causes activation of the source of light-based energy after the expiration of the first predetermined period of time to heat hair follicles in the area of skin tissue containing hair follicles to one of: above 55 degrees C., 60 degrees C., 65 degrees C. or 70 degrees C. for a second predetermined period of time, wherein the second predetermined period of time is less than the first predetermined period of time.

In another aspect, the first predetermined period of time is in the range of about 1 second to about 15 minutes and the second predetermined period of time is less than about 1 second. The source of ultrasonic energy and the source of light-based energy may be contained within a unitary housing, the unitary housing having a surface placed in contact with the skin tissue at least during activation of the source of ultrasonic energy and the source of light-based energy. A device to cool the skin tissue may be positioned in the unitary housing during one or more of activations of the ultrasonic energy source and the light-based energy source. The ultrasonic source of energy may provide the energy at 200 KHz to 5 MHz.

DETAILED DESCRIPTION OF THE PRESENT INVENTION

Figure 1:
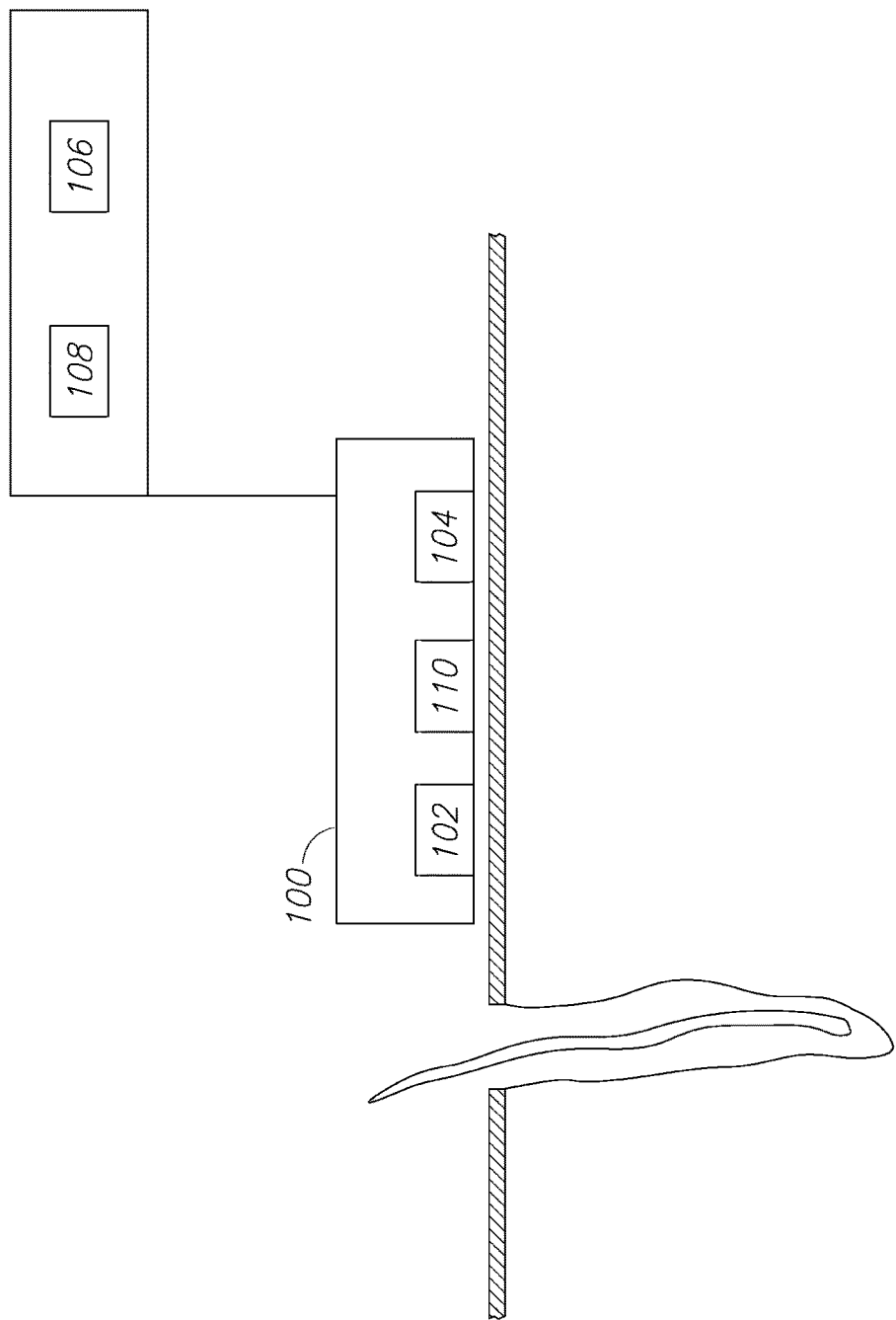
FIG. 1 illustrates a first embodiment of the present invention.

Turning first to FIG. 1, that figure illustrates a first embodiment of a device 100 which includes both a light energy source and a source of ultrasound energy. The ultrasound source 102 produces ultrasound energy that preheats the bulk area from which hair is to be removed to at least 43° C. and up to 50° C. Once the bulk area and the follicles within the bulk area have been preheated, a light energy source 104, either of a coherent or incoherent nature, may irradiate on the hair follicles just immediately after ultrasound treatment to cause a further increase in the temperature in the hair follicle or of the epidermis up to the damage threshold. According to this embodiment of the invention, the preheating ultrasound phase is non-selective and non-pigmented based while the succeeding light phase may be selective to target pigmented hair which absorbs the extra amount of energy delivered from light source 104.

A two-step treatment preheats the bulk of the target tissue to a sub-threshold level where there is minimal or no damage to hair follicles in a short period of less than a few seconds (as mentioned above, long durations of heating even at these sub-threshold levels to an about 1 seconds to 15 minutes may also damage the follicles). As a second step, light source 104 is configured to deliver the extra amount of energy so that at least the follicle areas in the target tissue reach an energy level which is above the threshold to damage the follicles. The ultrasonic first phase may be configured to raise the bulk of the target tissue to a temperature in the range of approximately 43-55 degrees centigrade or more specifically to a range of 43-50 degrees centigrade.

The second, optical phase is configured to raise the temperature of the follicles located within the preheated target bulk tissue to a temperature above 55 degrees centigrade or to a temperature above 60, or 65 or 70 degrees centigrade for time periods of less than 1 second.

According to one aspect of this embodiment, due to the non-selective preheating of the bulk of the tissue, once a selective hair targeting is provided in the second optical phase and extra heat is absorbed by the hair, it experiences smaller thermal gradient and as a result more heat can be confined in the hair before damaging the surrounding tissue in the vicinity of the hair follicle. The slower thermal diffusion enables providing, during the second optical phase, longer pulses above the regime of 3-30 msecs which are currently practiced without bulk heating.

The ultrasound energy provided can be focused, collimated or unfocused, each being able to provide the desired effect to the area to be treated. Both types of ultrasound, focused and unfocused, may be incorporated into the device 100. Different numbers and combinations of ultrasound sources and/or light sources may be provided as known to those skilled in the art.

The device 100 of FIG. 1 may also include a known type of programmable or programmed controller 106 to control the light and ultrasonic energy sources as well as an imaging device 108 to detect either a single hair follicle or plurality of follicles and to target them with ultrasound energy.

In addition, a cooling device 110 may be provided to provide cooling immediately before, after or simultaneously while treating the follicles. According to the ultrasound aspect of the invention, energy in the range of 200 kHz-5 MHz may be provided by the ultrasound transducers in a pulsed or continuous mode. While the sequence of application of energy described so far is first ultrasound and then light-based energy, it is to be understood that this may be reversed, with light-based first, then ultrasound, or even the sequence ultrasound/light/ultrasound or light/ultrasound/light, etc.

As mentioned above, when a follicle is heated in a selective pigment-based heating mechanism, heat diffuses to its surrounding skin tissue. Such a diffusion is a function of the temperature differences between the hair and the surrounding skin. A generalization of the amount of heat which diffuses may be described using the following relation between some of the relevant variables:

$$Q \alpha h * A_{area} * (T_{hair} - T_{skin})$$

Where Q is the amount of heat which diffuses and h is the heat transfer coefficient and A is the area through which the heat dissipates. $T_{hair}$ is the hair temperature and $T_{skin}$ is the skin temperature.

The smaller the $\Delta T$, the slower the heat diffuses from the follicle to the skin during the second optical phase of treatment. As mentioned above, treating fine hair is a challenge. One of the reasons for this challenge is due to the lack of pigments in the fine hair in general and facial fine hair in particular. However, another challenge is due to the fact that a thin hair has a shorter thermal relaxation time which means that more heat diffuses to the skin faster. As a result, it is a problem to accumulate heat in thin hair to the required level of damaging its follicle. One may see it as heat "leaking" from the hair into the surrounding skin. Therefore, it is one aspect of the present invention to raise the bulk temperature around thin hair and to then raise selectively the temperature of the thin hair so that it experiences a smaller $\Delta T$, heat diffusion is reduced, more heat is accumulated and follicle damage may be achieved. Such a follicle damage may be achieved by practicing pulses which are as long as 50 msec as will be shown below.

As mentioned above, the thinner the hair the shorter its thermal relaxation time. Thermal relaxation time (TRT) varies with hair diameter according to the following relation:

$$TRT \alpha D^2_{hair}/4*K$$

Where D is the hair diameter and K is the thermal diffusivity which is $\sim 1.3*10^{-3}$ cm/sec.

Comparing TRT of a hair having a diameter of 20μ to hair having a diameter of 100μ is:

$$TRT_{20\mu}/TRT_{100\mu} \alpha (20/100)^2 = 1/25$$

Therefore, $$25 * TRT_{20\mu} = TRT_{100\mu}$$

The thinner the hair is, the shorter the TRT of the hair. However since $T_{hair} \alpha TRT$ Therefore, the thinner the hair, the smaller the amount of heat accumulated in the hair, $T_{hair}$ (the light is "less effective" in heating the hair, lot of heat "leaks" to the skin). As a result, in order to be able to raise the temperature of such a thin hair, a shorter pulse may be provided. A YAG Laser for example may produce 50 Joules per pulse. If the pulse is, for example, 5 msec, the peak power is about 10,000 Watt which is sufficient to damage the follicle. However, since laser diodes cannot provide 50 Joules at such a short pulse of 5 msec they cannot be used in such circumstances to damage the follicles. However, laser diodes may reach 50 Joules in a pulse duration of about 50 msec. This may provide a peak power of about 1,000 Watt which is less than the amount of heat needed to damage the follicle. Laser diodes cannot provide such a short pulse of 5 msec as the YAG with such a high energy.

It is therefore another aspect of the present invention to provide the preheating phase according to one aspect of the invention. The preheating phase reduces ΔT and therefore diffusivity K is also reduced. A smaller diffusivity increases TRT. In other words, a preheating phase induces an effective longer TRT on a thin hair. The longer TRT allows using longer pulses while still accumulating heat within a thin hair and its follicle. Under these conditions, tissue pre-heating followed by a long diode laser heating pulse may be confined into a thin hair follicle causing the required thermal damage.

Figure 2:
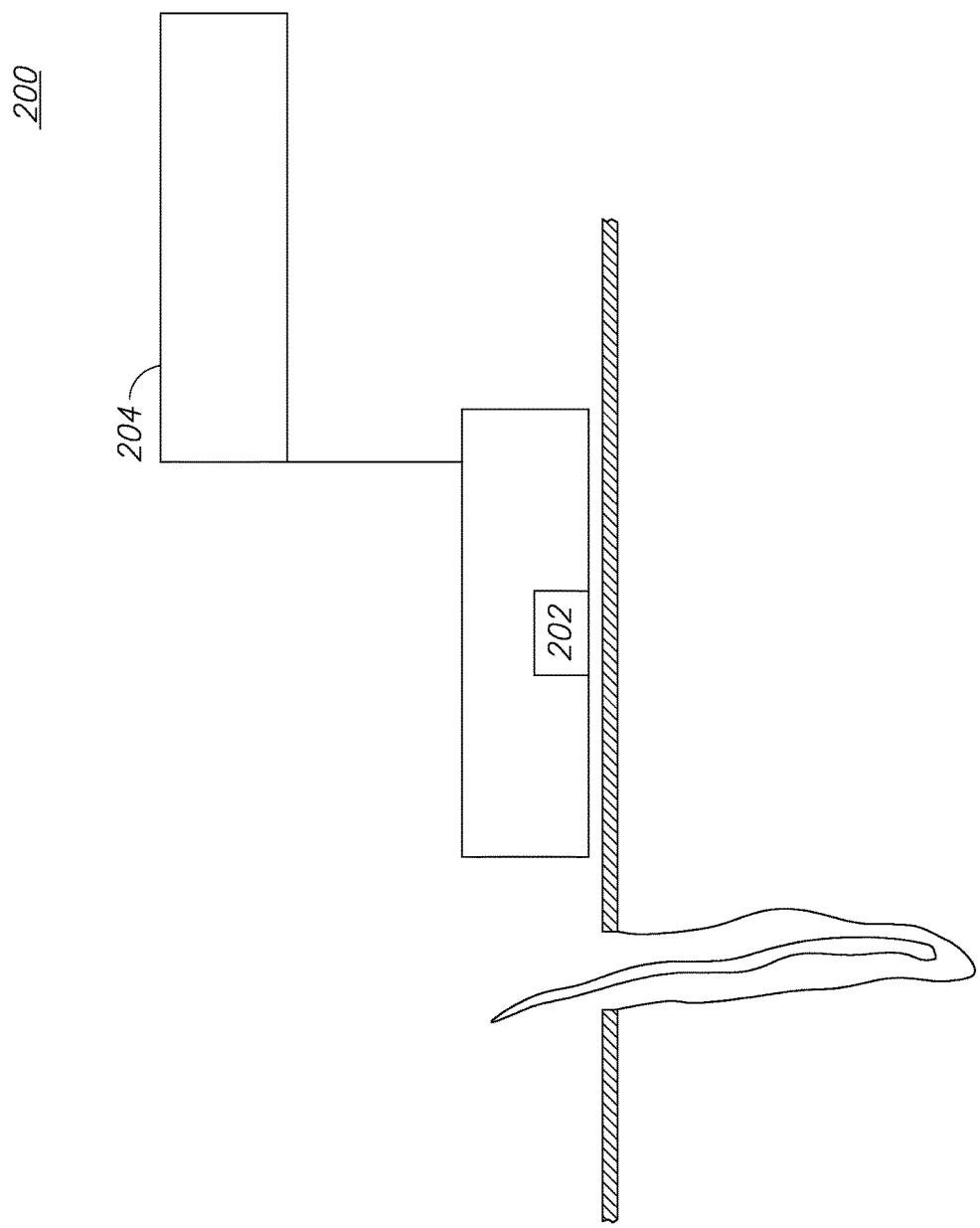
FIG. 2 illustrates a second embodiment of the present invention.

Turning now to FIG. 2, this figure illustrates a second embodiment 200 which includes a source of ultrasonic energy 202 alone to heat the hair follicles, either single or plurality, to a temperature between 42° C. to 50° C. under control of a controller 204. This temperature may be maintained for a certain amount of time, that is, from about a few seconds to about 1-15 minutes to achieve an appropriate temperature at the hair follicle or to reach the damage threshold of the hair follicle. As in the first embodiment of FIG. 1, the ultrasonic source may be focused, collimated or focused and work under similar characteristics as described above.

Figure 3:
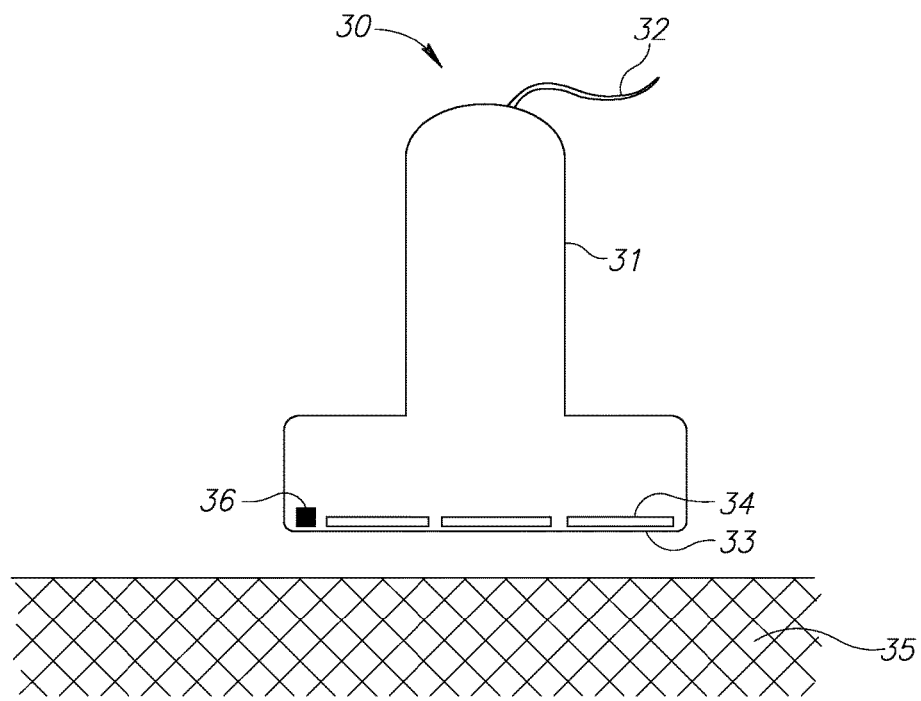
FIG. 3 illustrates a first embodiment of an ultrasound handpiece.

Turning now to FIG. 3, that figure shows an embodiment which, like that of FIG. 2, contains only ultrasound energy source(s). The ultrasound energy provided can be focused, collimated or unfocused, each being able to provide the desired effect to the area to be treated. Both types of ultrasound, focused and unfocused, may be incorporated into the device 30. Unfocused ultrasound may be provided by one or more ultrasound transducers 34 which are applied to the skin tissue topically using the hand held device 30 having ultrasound transducers located on a plane 33 which is parallel to a patient's skin 35, as shown in FIG. 3.

Figure 4:
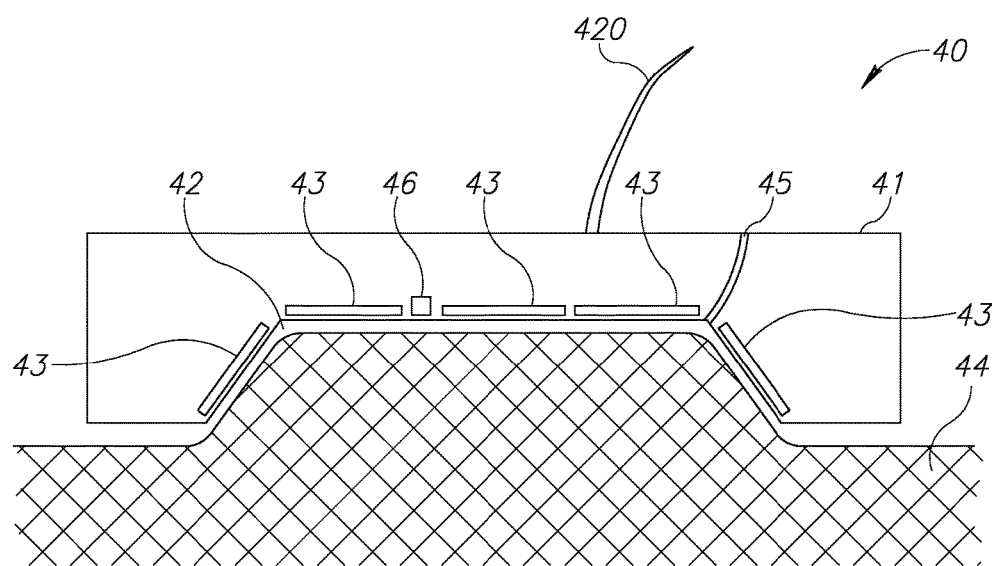
FIG. 4 illustrates a second embodiment of an ultrasound handpiece.

Alternatively, as illustrated in FIG. 4, a probe 40 may be provided with a cavity 42 and a negative pressure input port 45 which is configured to pull skin 44 into cavity 42 in order to couple skin 44 to at least one of the ultrasound sources 43 shown in FIG. 4. The number of sources 43 may vary and may be positioned either parallel or generally perpendicular to the skin surface. Alternatively, light sources may be "mixed and matched" with ultrasound sources in the probe 40 of FIG. 4. Different numbers and combinations of ultrasound sources and/or light sources may be provided as known to those skilled in the art.

According to yet another embodiment of the invention, a single or multiple ultrasound and/or light sources may be attached to a scanning arm within probe 30 or 40 of FIG. 3 or FIG. 4 respectively in order to scan an area of a tissue underneath the probe. According to this embodiment, focused ultrasound may be used to scan an area of a target tissue in order to raise its temperature in the preheating first phase of treatment as discussed above.

Probe 30 of FIG. 3 may also be used to provide continuous ultrasound in a "painting" mode in which the physician may slide the probe on a target treated area which is bigger than area 33 of the probe to build up the temperature in this area. Probe 40 of FIG. 4, however, may be best used for practicing a stamping mode of treatment in which the probe is placed stationary over a target tissue, a negative pressure source which is configured to be in fluid communication with channel 45 protrudes the target tissue into cavity 42 and the energy sources are activated to produce the first bulk pre-heating phase followed by a second selective treatment phase.

According to another embodiment of the present invention, at least one temperature sensor 36 (FIG. 3) or 46 (FIG. 4) may be configured to measure the skin temperature underneath the probe and to feed back the information to a main console through umbilicals 32 or 420 respectively. In a pulse mode, the transducers may be configured to provide pulses of about 10 msec to 10 sec. A temperature sensor may also be positioned in either or both of the units 100 or 200 of FIGS. 1 and 2 respectively and temperature readings fed back to the controllers in each of the units. The temperature reading back may be utilized by the controller to regulate the activation of the ultrasound and/or light-based energy sources.

I claim:

1. A cosmetic method for the removal of hair from the skin tissue of a human body comprising:
   providing a device that includes a source of ultrasound energy and a source of light-based energy;
   activating the source of ultrasound energy and providing the ultrasound energy to the skin tissue to heat an area of skin tissue containing hair follicles from 43 degrees C. to about 55 degrees C.;
   continuing the providing of ultrasound energy for a first predetermined period of time;
   activating the source of light-based energy after the expiration of the first predetermined period of time to heat hair follicles in the area of skin tissue containing hair follicles to one of: above 55 degrees C., 60 degrees C., 65 degrees C. or 70 degrees C. for a second predetermined period of time, wherein the second predetermined period of time is less than the first predetermined period of time;
   wherein the first predetermined period of time is in the range of 1 second to 15 minutes; and
   wherein the second predetermined period of time is less than 1 second.

2. The cosmetic method of claim 1 further comprising a controller to control the activation of the source of ultrasonic energy and the source of light-based energy and the first and second predetermined periods of time.

3. The cosmetic method of claim 1 wherein the source of ultrasonic energy and the source of light-based energy are contained within a unitary housing, the unitary housing having a contact surface, wherein the contact surface is configured to be placed in contact with the skin tissue at least during activation of the source of ultrasonic energy and the source of light-based energy.

4. The cosmetic method of claim 3, further comprising cooling the skin tissue with a cooling device in the unitary housing during one or more of activations of the ultrasonic energy source and the light-based energy source.

5. The cosmetic method of claim 3, wherein the contact surface is shaped to form a cavity, and a source of negative pressure draws the skin tissue into the cavity to draw the tissue closer to one or more of the source of ultrasonic energy or the source of light-based energy.

6. The cosmetic method of claim 1 further comprising an imaging device to provide images of hair follicles to be targeted by one or more of ultrasonic energy or light-based energy.

7. The cosmetic method of claim 1 wherein the ultrasonic source of energy provides the energy at 200 KHz to 5 MHz.

8. The cosmetic method of claim 1 wherein the light-based source of energy is a laser energy source.

9. The cosmetic method of claim 1, further comprising the step of measuring the temperature of the skin tissue one or more of: before, during or after the providing of one or more of ultrasonic energy or light-based energy to the skin tissue.

10. An apparatus for the removal of hair from the skin tissue of a human body comprising:
   a source of ultrasound energy and a source of light-based energy;
   a controller programmed to activate one or more of the sources of ultrasound energy and light-based energy for first and second predetermined periods of time;
   the controller causing activation of the source of ultrasound energy and causing the source of ultrasound energy to be provided to the skin tissue to heat an area of skin tissue containing hair follicles from 43 degrees C. to 55 degrees for the first predetermined period of time;
   the controller causing activation of the source of light-based energy after the expiration of the first predetermined period of time to heat hair follicles in the area of skin tissue containing hair follicles to one of: above 55 degrees C., 60 degrees C., 65 degrees C. or 70 degrees C. for a second predetermined period of time, wherein the second predetermined period of time is less than the first predetermined period of time.

11. The apparatus of claim 10 wherein the first predetermined period of time is in the range of 1 second to 15 minutes.

12. The apparatus method of claim 10, wherein the second predetermined period of time is less than 1 second.

13. The apparatus of claim 10 wherein the source of ultrasonic energy and the source of light-based energy are contained within a unitary housing, the unitary housing having a contact surface, wherein the contact surface is configured to be placed in contact with the skin tissue at least during activation of the source of ultrasonic energy and the source of light-based energy.

14. The apparatus of claim 13, further comprising a device to cool the skin tissue positioned in the unitary housing during one or more of activations of the ultrasonic energy source and the light-based energy source.

15. The apparatus of claim 10 wherein the ultrasonic source of energy provides the energy at 200 KHz to 5 MHz.

16. The apparatus of claim 10 wherein the light-based source of energy is a laser energy source.

* * * * *